(12) United States Patent
Laborde et al.

(10) Patent No.: US 6,894,054 B2
(45) Date of Patent: May 17, 2005

(54) HETEROCYCLIC INHIBITORS OF GLYCINE TRANSPORTER 2

(75) Inventors: Edgardo Laborde, Foster City, CA (US); Hugo O. Villar, La Jolla, CA (US)

(73) Assignee: Telik, Inc., Palo Alto, CA (US)

( * ) Notice: Subject to any disclaimer, the term of this patent is extended or adjusted under 35 U.S.C. 154(b) by 68 days.

(21) Appl. No.: 10/072,308

(22) Filed: Feb. 5, 2002

(65) Prior Publication Data

US 2003/0073726 A1 Apr. 17, 2003

Related U.S. Application Data

(60) Provisional application No. 60/267,894, filed on Feb. 9, 2001.

(51) Int. Cl.[7] ............... A61K 31/433; A61K 31/497
(52) U.S. Cl. ............ 514/255.05; 514/256; 514/262.1; 514/263.2; 514/307; 514/342; 514/363
(58) Field of Search .................... 514/363, 364, 514/384, 255.05, 342, 256, 262.1, 263.2, 307

(56) References Cited

U.S. PATENT DOCUMENTS

| | | | |
|---|---|---|---|
| 4,097,669 A | 6/1978 | Reisdorff et al. | ............ 542/413 |
| 4,325,959 A | 4/1982 | Matthews | ............ 31/425 |
| 5,587,293 A | 12/1996 | Kauvar et al. | ............ 435/7.21 |
| 5,668,159 A | 9/1997 | Jin | ............ 514/363 |
| 5,670,526 A | 9/1997 | Dodd et al. | ............ 514/340 |
| 5,756,348 A | 5/1998 | Smith et al. | ............ 435/325 |
| 5,968,823 A | 10/1999 | Borden et al. | ............ 435/349 |
| 6,008,015 A | 12/1999 | Albert et al. | ............ 435/69.1 |
| 6,127,131 A | 10/2000 | Smith et al. | ............ 435/7.1 |

FOREIGN PATENT DOCUMENTS

| | | |
|---|---|---|
| DE | 30 31 191 | 3/1981 |
| DE | 37 17 865 | 12/1988 |
| EP | 0 214 732 A2 | 3/1987 |
| EP | 0 276 793 A2 | 1/1988 |
| EP | 0 409 332 A2 | 1/1991 |
| EP | 0 554 107 A1 | 8/1993 |
| GB | 2 263 635 A | 8/1993 |
| JP | 11-043485 | 6/1989 |
| JP | 2-129173 | 5/1990 |
| JP | 7-005646 | 1/1995 |
| JP | 9-114055 | 5/1997 |
| JP | 10-036357 | 2/1998 |
| WO | WO 91/11909 | 8/1991 |
| WO | WO 95/13268 | 5/1995 |
| WO | WO 97/45115 | 12/1997 |
| WO | WO 97/45423 | 12/1997 |
| WO | WO 98/30561 | 7/1998 |
| WO | WO 99/44596 | 9/1999 |
| WO | WO 99/45011 | 9/1999 |
| WO | WO 01/57024 | 8/2001 |
| WO | WO 01/87855 | 11/2001 |

OTHER PUBLICATIONS

Gomeza et al. Glycine transporter isoforms in the mammalian central nervous sytem: Structrues, functions and therapeutic promises, Current Opinion in Drug Discovery and Development 6(5):675–682, 2003.*

Hazzaa et al., Synthesis and biological evalution of 3–quinolyl–5–mercapto–1,2,4–triazoles, *Sci Pharm*, 46(4), 298–306 (1978).

Gulerman et al., "Evaluation of antimycobacterial and anticonvulsant activities of new 1–(4–fluoro–benzoyl)–4–substituted–2,4–dihydro–3H–1,2, 4–triazole–3–thione derivatives", *II Farmaco*, 52(11), 691–695 (1997).

*Chem Abs*, 128(3), 22862 (1998); Abstract of Habib et al., "Synthesis and antimicrobial testing of novel oxadiazolyl-benzimidazole dericatives", *Pharmazie*, 52(10), 746–749 (1997).

*Biosis Database*, Abstract No. PREV200100076408 (2000); Abstract of Lechner et al., "Novel glycine transporter 2 inhibitors are analgesic in a rat model of inflammatory pain", *Soc Neurosci Abs*, 26(1–2), Abstract 150.18 (2000).

\* cited by examiner

*Primary Examiner*—Richard L. Raymond
(74) *Attorney, Agent, or Firm*—Cooley Godward LLP

(57) ABSTRACT

Compounds, compositions, and methods for inhibiting the glycine transporter 2 and for inhibiting glycine transporter mediated neuronal activity. These compounds are particularly useful for treating diseases of the nerve and muscle, including psychoses, pain, epilepsy, neurodegenerative diseases, stroke, head trauma, multiple sclerosis and the like, and of muscle disorders, including diseases or conditions associated with increased muscle contraction, such as spasticity and myoclonus. In addition, the compounds may be used to discover other agents with improved activity in assays in which the compounds of the invention are active.

2 Claims, No Drawings

HETEROCYCLIC INHIBITORS OF GLYCINE TRANSPORTER 2

CROSS-REFERENCE TO RELATED APPLICATIONS

This application claims the priority under 35 USC 119(e) of Provisional Application Ser. No. 60/267,894, filed Feb. 9, 2001, which is incorporated herein by reference.

BACKGROUND OF THE INVENTION

1. Field of the Invention

This invention relates to the treatment of certain central and peripheral nervous system disorders by inhibition of the glycine transporter 2. The invention relates in particular to the use of a group of compounds in the treatment in humans of certain neurological disorders, for example, psychoses, pain, epilepsy, neurodegenerative diseases, stroke, head trauma, multiple sclerosis and the like. The invention also relates to a group of novel compounds and pharmaceutical compositions containing them which are useful in inhibition of the glycine transporter 2.

2. Description of Related Art

Synaptic transmission is a complex form of intercellular communication that involves a considerable array of specialized structures in both the pre- and post-synaptic neuron. High affinity neurotransmitter transporters are one such component, located on the pre-synaptic terminal membranes and surrounding glial cells (Kanner and Schuldiner, *CRC Critical Reviews in Biochemistry*, 22, 1032 (1987)). Transporters sequester neurotransmitter from the synapse, thereby regulating the concentration of neurotransmitter in the synapse, as well as its duration of action therein, which together influence the magnitude and duration of synaptic transmission. By preventing the spread of transmitter to neighboring synapses, transporters help maintain the fidelity of synaptic transmission. In addition, by sequestering released transmitter into the presynaptic terminal, transporters allow for transmitter reutilization.

The amino acid glycine is a major neurotransmitter in the mammalian central nervous system (CNS), functioning at both inhibitory and excitatory synapses. These distinct functions of glycine are mediated by two different types of receptor, each of which is associated with a different class of glycine transporter. The inhibitory actions of glycine are mediated by glycine receptors that are sensitive to the convulsant alkaloid strychnine, and are referred to "strychnine-sensitive." Such receptors contain an intrinsic chloride channel that is opened upon binding of glycine to the receptor; by increasing chloride conductance, the threshold for firing of an action potential is increased. Strychnine-sensitive glycine receptors are found predominantly in the spinal cord and brainstem, and pharmacological agents that enhance the activation of such receptors will thus increase inhibitory neurotransmission in these regions. For example, enhancing inhibitory glycinergic transmission through strychnine-sensitive glycine receptors in the spinal cord can be used to decrease muscle hyperactivity. In addition, pain-related information in the spinal cord has been shown to be mediated by these receptors (Yaksh, *Pain*, 37, 111 (1989)).

Nucleic acid sequences and transfection techniques for delivering nucleic acid message coding for glycine transporters are disclosed in U.S. Pat. No. 5,756,348, U.S. Pat. No. 6,127,131, U.S. Pat. No. 5,824,486, U.S. Pat. No. 5,968,823, and U.S. Pat. No. 6,008,015. Molecular cloning has revealed the existence in mammalian brains of two classes of glycine transporters, termed GlyT1 and GlyT2. GlyT1 is found predominantly in the forebrain, and its distribution corresponds to that of glutaminergic pathways and NMDA receptors (Smith et al., *Neuron*, 8, 927 (1992)). Additional cloning experiments has determined that GlyT1 transporter has three additional variants, GlyT1a, GlyT1b, and GlyT1c. GlyT2 is found predominantly in the brain stem and spinal cord, and its distribution corresponds closely to that of strychnine-sensitive glycine receptors. This is consistent with the view that by regulating the synaptic levels of glycine, GlyT1 and GlyT2 selectively influence the activity of the NMDA receptors and strychnine-sensitive glycine receptors, respectively.

Triazoles, oxadiazoles, and thiadiazoles are known in the art. They have shown a wide variety of uses in photographic material (JP 09-114055, JP 07-005646) and in liquid crystal compositions (JP 11-043485). These types of heterocyclic derivatives have also been reported as pesticides, fungicides and herbicides (JP 10-036357, JP 05-202038, JP 02-129173, DE 3717865, DE 3031191, DE 2533605). There are a number of highly functionalized analogs showing activity as immunosuppressants, antiinflammatories and hepatoprotectants (U.S. Pat. No. 5,670,526, EP 214732), Gp IIb/IIIa antagonists (U.S. Pat. No. 5,668,159), antiulcer (WO 95/13268) and as angiotensin II antagonists (EP 554107, WO 91/11909, EP 409332).

Substituted triazoles have been reported to be neurotensin antagonists and be useful in the treatment of certain CNS and gastrointestinal disorders (GB 2263635, WO 98/30561). Recently, there have been some reports of piperidinyl-, and piperazinyl-triazoles as inhibitors of the glycine transporters (WO 99/45011, WO 99/44596); and diarylglycine derivatives have been shown to inhibit GlyT1 and GlyT2 (WO 97/45115).

The documents cited here and elsewhere in this application are incorporated herein by reference in their entirety.

SUMMARY OF THE INVENTION

The inventors have discovered and herein disclose that the triazoles, oxadiazoles, and thiadiazoles inhibit the glycine transporter 2 (GlyT2) and are useful in the regulation of the central and peripheral nervous systems. Thus, the invention is directed to methods for inhibiting GlyT2 in mammals using these triazoles, oxadiazoles, and thiadiazoles, or pharmaceutical compositions containing them. The compounds, compositions and methods of the invention are particularly useful in the treatment of diseases of nerve and muscle.

Inhibition of GlyT2 diminishes the activity of neurons having strychnine-sensitive glycine receptors via increasing synaptic levels of glycine. Inhibition of glycine transporters by the triazoles, oxadiazoles, and thiadiazoles is effective to alter receptor function, and can be used to provide therapeutic benefits in a variety of disease states, including diseases of muscles and of the nervous system. Thus, for example, these compounds may be used to diminish the transmission of pain-related information in the spinal cord, to decrease muscle hyperactivity, to treat neurological disorders such as psychoses, pain, epilepsy, neurodegenerative diseases, stroke, head trauma, multiple sclerosis and the like, and to treat diseases or conditions associated with increased muscle contraction, such as spasticity and myoclonus.

In a first aspect, this invention is a method of treating a disease treatable by the inhibition of the glycine transporter 2 (GlyT2) by administering a therapeutically effective amount of a compound of Formula I:

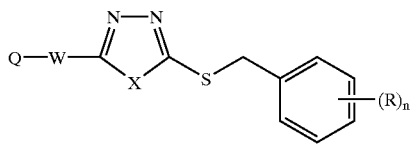

Formula I where:
n is 0, 1, 2 or 3;
each R is independently halogen, hydroxy, lower alkyl optionally substituted with halogen, or lower alkoxy optionally substituted with halogen;
X is O, S or N—R' (where R' is lower alkyl aryl, heteroaryl, aryl-lower alkylene or heteroaryl-lower alkylene);
Q is optionally present, and when present is of the formula:

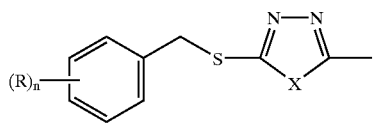

in which n, R, and X are as defined above;
when Q is present, W is a lower alkylene, and
when Q is absent, W is optionally substituted lower alkyl, optionally substituted aryl, optionally substituted heteroaryl, (optionally substituted aryl)-X—CH$_2$— or (optionally substituted heteroaryl)-X—CH$_2$— in which X is as defined above,
or a pharmaceutically acceptable salt thereof.

More specifically, in the first aspect, this invention is directed to the treatment of neurological disorders, including psychoses, pain, epilepsy, neurodegenerative diseases, stroke, head trauma, multiple sclerosis and the like, and of muscle disorders, including diseases or conditions associated with increased muscle contraction, such as spasticity and myoclonus, in a mammal, especially a human, by administering a therapeutically effective amount of a compound of Formula I, a pharmaceutically acceptable salt therof, to the mammal. Optionally, the treatment also comprises administering an additional conventional therapy for the condition being treated.

In a second aspect, this invention is compounds of Formula II:

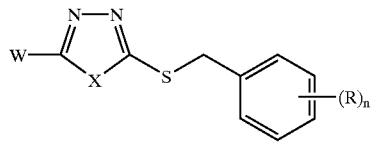

Formula II where:
each R is independently halogen, hydroxy, lower alkyl optionally substituted with halogen or lower alkoxy optionally substituted with halogen;
X is S or N—R' (where R' is lower alkyl, aryl, heteroaryl, aryl-lower alkylene, or heteroaryl-lower alkylene);
when X is S, n is 1, 2 or 3, and W is an optionally substituted heteroaryl having at least two heteroatoms, and
when X is N—R', n is 0, 1, 2 or 3, and W is (optionally substituted heteroaryl)-S—CH$_2$— where the heteroaryl has five ring atoms including one heteroatom;
and the pharmaceutically acceptable salts thereof.

In a third aspect, the invention is pharmaceutical compositions comprising a pharmaceutically acceptable excipient and, as an active ingredient, a compound of Formula II or a pharmaceutically acceptable salt thereof.

In a fourth aspect, the invention is a method of inhibiting GlyT2 in a cell containing GlyT2 comprising contacting a cell with a compound of Formula I, or a pharmaceutically acceptable salt thereof, in an amount sufficient to inhibit GlyT2. In vivo, the step of contacting the cells with such a compound may be effected by administering to an animal an effective amount of the compound. In vitro, the step of contacting the cells with a compound of Formula I may be effected by administering an effective amount of the compound to the cells or to a solution bathing the cells.

Other aspects of the invention include methods for discovering agents which show improved activity in assays that inhibit GlyT2 or affect GlyT2-mediated neuronal activity.

DETAILED DESCRIPTION OF THE INVENTION (a) Definitions and General Parameters "Alkyl" means a $C_1$–$C_{20}$ monovalent hydrocarbyl which may be linear, branched, or cyclic. "Lower alkyl", as in "substituted lower alkyl", means a $C_1$–$C_{10}$ alkyl. "Lower alkyl" includes methyl, ethyl, isopropyl, propyl, butyl, isobutyl, sec-butyl, tert-butyl, pentyl, hexyl, cyclopentyl, cyclopropylmethyl, cyclohexyl, and cyclohexylmethyl. $C_1$–$C_6$ lower alkyls are preferred.

A "substituted lower alkyl" is a lower alkyl which is mono-, di-, or tri-substituted with aryl, R'-substituted aryl, heteroaryl, nitro, cyano, halo, —OR, —SR, —COR, —OC(O)R, —C(O)OR, —NR$_2$, —SO$_2$OR, —OSO$_2$R, —SO$_2$NR$_2$, —NRSO$_2$R, —CONR$_2$, or —NRCOR, where each R is, independently, hydrogen, lower alkyl, R'-substituted lower alkyl, aryl, R'-substituted aryl, heteroaryl, heteroaryl(lower)alkyl, R'-substituted aryl (lower)alkyl, or aryl(lower)alkyl and each R' is, independently, hydroxy, halo, lower alkyloxy, cyano, thio, nitro, lower alkyl, halo-lower alkyl, or amino. Substituted lower alkyls which are substituted with substituents selected from the group consisting of cyano, halo, lower alkyloxy, thio, nitro, amino, or hydroxy are particularly preferred.

"Alkoxy" or "alkyloxy" means —OR where R is alkyl, e.g., ($C_{1-4}$)alkyloxy includes the radicals methoxy, ethoxy, prop-1-yloxy, prop-2-yloxy, but-1-yloxy, but-2-yloxy, 2-methylprop-1-yloxy and 2-methylprop-2-yloxy.

An "alkylene" group is a divalent hydrocarbyl of the formula, —$C_nH_{2n}$—, which may be straight or branched. It includes methylene (—CH$_2$—), ethylene (—$C_2H_4$—), n-propylene (—$C_3H_6$—) and n-butylene (—$C_4H_8$—).

"Aryl" means a monovalent aromatic hydrocarbyl containing 6 to 20 ring carbon atoms, having a single ring (e.g., phenyl), or two or more condensed rings, preferably 2 to 3 condensed rings (e.g., naphthyl), or two or more aromatic rings, preferably 2 to 3 aromatic rings, which are linked by a single bond (e.g., biphenylyl). Optionally, the aryl group may be substituted with lower alkyl, substituted lower alkyl, aryl, heteroaryl, nitro, cyano, halo, —OR, —SR, —COR, —OC(O)R, —C(O)OR, —NR$_2$, —SO$_2$OR, —OSO$_2$R, —SO$_2$NR$_2$, —NRSO$_2$R, —CONR$_2$, or —NRCOR; where each R is independently, hydrogen, lower alkyl, substituted lower alkyl. Aryl groups are preferably $C_6$–$C_{16}$ and even more preferably, $C_6$ to $C_{14}$.

"Heteroaryl" means a monovalent aromatic radical containing 5–14 ring atoms, 1–5 of which are hetero atoms selected from a group consisting of N, O and S, and includes monocyclic, condensed heterocyclic and condensed carbocyclic and heterocyclic aromatic rings (e.g., thienyl, furyl, pyrrolyl, pyrimidinyl, isoxazolyl, oxazolyl, indolyl, benzo[b]thienyl, isobenzofuranyl, purinyl, isoquinolyl, pteridinyl, imidazolyl, pyridyl, pyrazolyl, pyrazinyl, etc.). Preferred heteroaryl groups are monocyclic 5- or 6-membered rings containing 1 or 2 heteroatoms.

A "substituted heteroaryl" is a heteroaryl substituted with lower alkyl, substituted lower alkyl, aryl, heteroaryl, nitro, cyano, halo, —OR, —SR, —COR, —OC(O)R, —C(O)OR, —NR$_2$, —SO$_2$OR, —OSO$_2$R, —SO$_2$NR$_2$, —NRSO$_2$R, —CONR$_2$, or —NRCOR; where each R is independently, hydrogen, lower alkyl or substituted lower alkyl.

"Halogen" or "halo" means fluoro, chloro or bromo.

A "pharmaceutically acceptable salt" may be any salt derived from an inorganic or organic acid or an inorganic or organic base. The term "pharmaceutically acceptable anion" refers to the anion of such acid addition salts. The term "pharmaceutically acceptable cation" refers to a cation formed by addition of a base. The salt and/or the anion or cation are chosen not to be biologically or otherwise undesirable.

A "therapeutically effective amount" means that amount which, when administered to an animal for treating a disease, is sufficient to effect such treatment for the disease.

"Treating" or "treatment" of a disease in a mammal includes (1) preventing the disease from occurring in a mammal which may be predisposed to the disease but does not yet experience or display symptoms of the disease, (2) inhibiting the disease, i.e., arresting its development, (3) relieving symptoms of the disease, i.e., reducing the effects of the disease, and (4) causing regression of the disease.

(b) Inhibition of Glycine Transporter-2

In a first aspect, this invention is a method of treating a disease treatable by the inhibition of the glycine transporter 2 (GlyT2) by administering a therapeutically effective amount of a compound of Formula I:

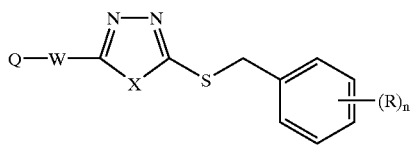

Formula I where:
n is 0, 1, 2 or 3;
each R is independently halogen, hydroxy, lower alkyl optionally substituted with halogen, or lower alkoxy optionally substituted with halogen;
X is O, S or N—R' (where R' is lower alkyl, aryl, heteroaryl, aryl-lower alkylene or heteroaryl-lower alkylene);
Q is optionally present, and when present is of the formula:

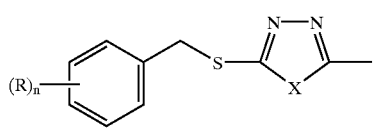

in which n, R and X are as defined above;
when Q is present, W is a lower alkylene, and
when Q is absent, W is optionally substituted lower alkyl, optionally substituted aryl, optionally substituted heteroaryl, (optionally substituted aryl)-X—CH$_2$— or (optionally substituted heteroaryl)-X—CH$_2$— in which X is as defined above,
or a pharmaceutically acceptable salt thereof.

GlyT2 inhibition is useful, for example, in the treatment of subjects with certain central and peripheral nervous system disorders, and in treatment of subjects with certain muscle disorders. More particular, examples of the use of the compounds include the treatment of psychoses, pain, epilepsy, neurodegenerative diseases, stroke, head trauma, multiple sclerosis and the like.

One embodiment of the invention is directed to a method of inhibiting GlyT2. This method comprises contacting a cell having a glycine transporter with a compound of Formula I, or a pharmaceutically acceptable salt thereof, in an amount sufficient to inhibit GlyT2. By inhibiting GlyT2, neuronal transmission is regulated and is useful in the treatment of psychoses, pain, epilepsy, neurodegenerative diseases, stroke, head trauma, multiple sclerosis, spasticity, myoclonus, or other disease condition. The inhibition of GlyT2 may occur either in vivo or in vitro. The contacting is effected in vivo by administering the compound/salt, or a pharmaceutical composition thereof, to the mammal and in vitro by administering the compound/salt, or a pharmaceutical composition thereof, to a container in which the cells are present or to a solution bathing the cells.

A further embodiment of the invention provides a method of treating a disorder in a mammal, where the disorder may be selected from a nervous disorder and a muscle disorder, comprising administering a therapeutically effective amount of a compound of Formula I, or a pharmaceutically acceptable salt thereof, to the mammal. Optionally, the method may further comprise treating the mammal with an additional form of therapy for such disease. For instance, one method may also comprise administering to the mammal a compound having pharmacological activity affecting the central nervous system (CNS) in addition to the compound of Formula I/salt. Alternatively, the compound of Formula I/salt may be administered to the mammal in combination with a CNS-active compound or other alternative treatment for nervous system disease. For the treatment of muscular conditions, the method may also comprise administering to the mammal a compound having pharmacological activity affecting muscle in addition to the compound of Formula I/salt. Alternatively, the compound of Formula I/salt may be administered to the mammal in combination with a muscle-active compound or other alternative treatment for muscular disease. The total amount of the combination of drugs administered to the mammal must be a therapeutically effective amount, although the individual amounts of each of the individual drugs may be, by themselves, suboptimal for therapeutic purposes.

Preferred compounds of Formula I include compounds/pharmaceutically acceptable salts where:
(i) X is N—R', where R' is methyl, ethyl, phenyl, or benzyl;
n is 0, 1 or 2;
R is chlorine or methyl;
Q is absent and W is aryl such as phenyl, optionally substituted heteroaryl such as
2-ethyl-5-methyl-3-diazolyl, or (optionally substituted heteroaryl)-X—CH$_2$—, such as thien-2-ylthiomethyl.

Examples of this group of compounds are:
3-[(2,6-dichlorophenyl)methylthio]-5-(thien-2-ylthiomethyl)-4-methyl-1,2,4-triazole,
3-benzylthio-5-(thien-2-ylthiomethyl)-4-methyl-1,2,4-triazole,
3-(4-methylbenzylthio)-5-(thien-2-ylthiomethyl)-4-methyl-1,2,4-triazole,
3-[(2,6-dichlorophenyl)methylthio]-5-(thien-2-ylthiomethyl)-4-ethyl-1,2,4-triazole,
3-benzylthio-5-(2-ethyl-5-methyl-3-diazolyl)-4-phenyl-1,2,4-triazole, and
3-[(2,6-dichlorophenyl)methylthio]-5-phenyl-4-benzyl-1,3,4-triazole.

(ii) X is S;
n is 0, 1, or 2;
R is chlorine;
Q is absent and W is aryl such as phenyl, or heteroaryl such as pyridyl or pyrazinyl.

Examples of this group of compounds are:
2-[(2,6-dichlorophenyl)methylthio]-5-(pyrazin-2-yl)-1,3,4-thiadiazole,
2-(benzylthio)-5-phenyl-1,3,4-thiadiazole,
2-(benzylthio)-5-(pyridin-3-yl)-1,3,4-thiadiazole,
2-[(2,6-dichlorophenyl)methylthio]-5-phenyl-1,3,4-thiadiazole, and
2-(benzylthio)-5-(pyrazin-2-yl)-1,3,4-thiadiazole.

(iii) X is O;
n is 0;
Q is present and in Formula Q, n is 0 and X is O; and
W is n-butylene.

The compound is 2,2'-(1,4-butanediyl)bis[5-(benzylthio)-1,3,4-oxadiazole].

Patients requiring treatment to inhibit GlyT2 include patients suffering from nervous disorders and patients suffering from muscle disorders. The method of treatment comprises the administration of an effective quantity of the chosen compound, preferably dispersed in a pharmaceutical carrier. A therapeutically effective dose of a compound of Formula I/salt is in the range of 0.01 to 1000 mg/kg, preferably 0.01 to 100 mg/kg and more preferably 1–30 mg/kg, but will be readily determined by one skilled in the art depending upon the route of administration, age and condition of the patient. The dosage units may be administered up to one to ten times daily for acute or chronic disease. No unacceptable toxicological effects are expected when compounds of Formula I/salts are administered in accordance with the present invention.

(c) Novel Compounds of the Invention

Another aspect of the present invention is compounds of Formula II:

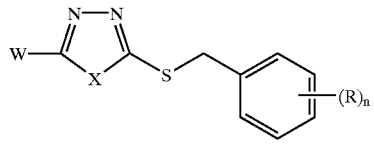

Formula II where:
each R is independently halogen, hydroxy, lower alkyl optionally substituted with halogen or lower alkoxy optionally substituted with halogen;
X is S or N—R' (where R' is lower alkyl, aryl, heteroaryl, aryl-lower alkylene, or heteroaryl-lower alkylene);
when X is S, n is 1, 2 or 3, and W is an optionally substituted heteroaryl having at least two heteroatoms, and
when X is N—R', n is 0, 1, 2 or 3, and W is (optionally substituted five-membered heteroaryl)-S—CH$_2$— where the five-membered heteroaryl comprises one heteroatom;
and the pharmaceutically acceptable salts thereof.

A preferred compound is the compound of Formula II in which X is S, n is 2, R is chlorine and W is pyrazin-2-yl, i.e. 3-[(2,6-dichlorophenyl)methylthio]-5-(pyrazin-2-yl)-1,2,4-triazole.

Compounds of Formula II have been found to inhibit GlyT2 and are useful for inhibiting GlyT2, including inhibiting GlyT2 in a mammal, especially a human, and for treating certain mammalian neurological disorders, in particular, psychoses, pain, epilepsy, neurodegenerative diseases, stroke, head trauma, multiple sclerosis and the like.

The compounds of Formula II, including the preferred compound described above, as single stereoisomers or mixtures of stereoisomers, and the pharmaceutically acceptable salts thereof, are suitable for use in pharmaceutical compositions for inhibiting GlyT2 in a mammal or for treating a mammal with certain neurological disorders, in particular, psychoses, pain, epilepsy, neurodegenerative diseases, stroke, head trauma, multiple sclerosis and the like.

(d) Synthesis of Compounds of Formulae I and II

The compounds of Formulae I and II may be prepared by synthetic methods known in the art. For example, they may be prepared according to the following reaction scheme:

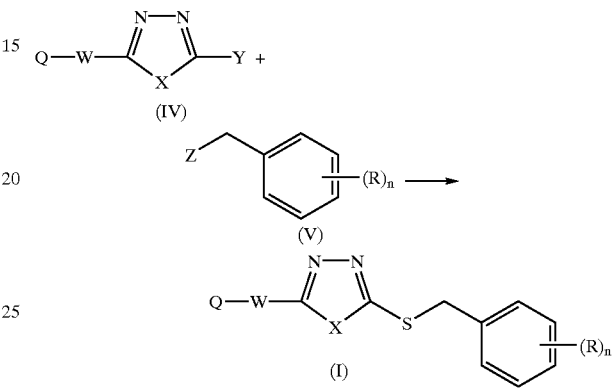

In the reaction scheme, Q, W, X, n and R are as defined above, one of Y and Z is mercapto or —SM (where M is an alkali metal, such as lithium, sodium, or potassium), and the other of Y and Z is a leaving group such as halogen, lower alkylsulfonyloxy, arylsulfonyloxy, or aralkylsulfonyloxy.

The reaction between the compounds of Formula IV and V may be carried out in a suitable solvent in the presence of a basic compound. Any inert solvent can be used as the solvent for the reaction. Examples of the solvent are disclosed in U.S. Pat. No. 5,670,526, and include water, alcohols, aromatic hydrocarbons, ethers, ketones, esters, aprotic solvents, and mixtures thereof. Examples of the basic compounds which can be used may also be found in U.S. Pat. No. 5,670,526. The reaction is carried out usually at 0–150° C., preferably at about 0–120° C., and completed in about 1 to 30 hours. The compound of Formula IV is usually used in an amount of at least one mole, preferably 1–12 moles, per mole of compound of Formula V.

The compounds of Formula V are usually commercially available. The compounds of Formula IV are either commercially available or may be synthesized by cyclization of a hydrazide. In the case of oxadiazole compounds, the cyclization of the hydrazide compounds may be carried out in the presence of CS$_2$ and a basic compound such as KOH. For the thiadiazole compounds, the cyclization of the hydrazide may be carried out in the presence of Lawesson's reagent, CS$_2$, and a basic compound. These syntheses are demonstrated in the examples below.

In some cases, protective groups may be introduced and later removed in the synthesis. Suitable protective groups for amino, hydroxyl, carboxyl groups are described in Greene et al., "Protective Groups in Organic Synthesis", 2nd ed., 1991, John Wiley and Sons, New York, N.Y. The compounds may be synthesized as shown in the examples below or by modifying the exemplified syntheses by means known to those of ordinary skill in the art.

Certain compounds of Formulae I and II may contain one or more chiral centers. In such cases, all stereoisomers also fall within the scope of this invention. The compounds include the individually isolated stereoisomers as well as mixtures of such stereoisomers.

Pharmaceutically acceptable salts, cations and anions of the compounds of Formulae I and II are also included in the present invention and are useful in the methods and pharmaceutical compositions described herein.

Pharmaceutically acceptable salts include salts which may be formed when acidic protons present are capable of reacting with inorganic or organic bases. Typically, the parent compound is treated with an excess of an alkaline reagent, such as hydroxide, carbonate or alkoxide, containing an appropriate cation. Cations, such as $Na^+$, $K^+$, $Ca^{2+}$, $Mg^{2+}$ and $NH_4^+$, are examples of cations present in pharmaceutically acceptable salts. The $Na^+$ salts are especially useful. Acceptable inorganic bases, therefore, include aluminum hydroxide, calcium hydroxide, potassium hydroxide, sodium carbonate and sodium hydroxide. Salts may also be prepared using organic bases, such as salts of primary, secondary and tertiary amines, substituted amines including naturally-occurring substituted amines, and cyclic amines including isopropylamine, trimethylamine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, N-ethylpiperidine, and the like.

If the compounds of Formulae I and II contain a basic group, an acid addition salt may be prepared. Acid addition salts of the compounds are prepared in a standard manner in a suitable solvent from the parent compound and an excess of acid, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluenesulfonic acid, hexanoic acid, heptanoic acid, cyclopentanepropionic acid, lactic acid, o-(4-hydroxy-benzoyl)benzoic acid, 1,2-ethanedisulfonic acid, 2-hydroxyethanesulfonic acid, benzenesulfonic acid, p-chlorobenzenesulfonic acid, 2-naphthalenesulfonic acid, camphorsulfonic acid, 4-methyl-bicyclo[2.2.2.]oct-2-ene-1-carboxylic acid, glucoheptonic acid, gluconic acid, 4,4'-methylenebis(3-hydroxy-2-naphthoic)acid, 3-phenylpropionic acid, trimethylacetic acid, t-butylacetic acid, laurylsulfuric acid, glucuronic acid, glutamic acid, 3-hydroxy-2-naphthoic acid, stearic acid, muconic acid and the like.

Certain of the compounds may form inner salts or zwitterions.

(e) Pharmaceutical Compositions of Formula II

One aspect of the invention is pharmaceutical compositions comprising a pharmaceutically acceptable excipient and, as an active ingredient, a compound of Formula II or a pharmaceutically acceptable salt thereof.

A preferred pharmaceutical composition for this use comprises, as the active ingredient, 2-[(2,6-dichlorophenyl) methylthio]-5-(pyrazin-2-yl)-1,3,4-thiadiazole.

The pharmaceutical compositions of this invention may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, 5% dextrose in water or buffered sodium or ammonium acetate solution. Such formulations are especially suitable for parenteral administration, but may also be used for oral administration. It may be desirable to add excipients such as polyvinylpyrrolidinone, gelatin, hydroxycellulose, acacia, polyethylene glycol, mannitol, sodium chloride or sodium citrate. Alternatively, these compounds may be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulation, and compressing, when necessary, for tablet forms; or milling, mixing and filling for hard gelatin capsule forms. When a liquid carrier is use, the preparation will be in the form of a syrup, elixir, emulsion or an aqueous or non-aqueous suspension. Such a liquid formulation may be administered orally directly or filled into a soft gelatin capsule.

Some specific examples of suitable pharmaceutical compositions are described in the Examples below.

Typically, a pharmaceutical composition of the present invention is packaged in a container with a label, or instructions, or both, indicating the use of the pharmaceutical composition in the treatment of nerve and muscle diseases, such as psychoses, pain, epilepsy, neurodegenerative diseases, stroke, head trauma, multiple sclerosis, spasticity, myoclonus, or other disease condition.

The compounds of Formulae I and II, or pharmaceutical compositions thereof, may be administered by any route suitable to the subject being treated and the nature of the subject's condition. Routes of administration include, but are not limited to, administration by injection, including intravenous, intraperitoneal, intramuscular, and subcutaneous injection, by transmucosal or transdermal delivery, through topical applications, nasal spray, suppository and the like or may be administered orally. Formulations may optionally be liposomal formulations, emulsions, formulations designed to administer the drug across mucosal membranes or transdermal formulations. Suitable formulations for each of these methods of administration may be found, for example, in such standard references as Gennaro, ed., "Remington: The Science and Practice of Pharmacy", 20th ed., 2000, Lippincott, Williams & Wilkins, Philadelphia, Pa.

(f) Methods for Discovering Agents for Inhibition of Glycine Transporter

Bioassays for determining glycine transporter typically measure glycine or radioactively labeled glycine transporter into cells having a glycine transporter. Glycine transporters are normally found in many cell types, including neuronal and glial cells and cell lines. In addition, exogenous glycine transporters may be provided to cells by transfection techniques. Nucleic acid sequences and transfection techniques for delivering nucleic acid message coding for glycine transporters are disclosed in U.S. Pat. No. 5,756,348, U.S. Pat. No. 6,127,131, U.S. Pat. No. 5,824,486, U.S. Pat. No. 5,968,823, and U.S. Pat. No. 6,008,015. Other bioassay methods for measuring glycine transporter include electrophysiological methods for measuring the strength and duration of neurotransmission at glycine synapses, both in vivo and in vitro. Such techniques, known in the art, include intracellular recording, patch clamp recording, and extracellular recording techniques. These electrophysiological techniques are also suitable for measuring the affects of glycine and other compounds on glycine transporter mediated neuronal activity. The use of such bioassays, in the presence of various concentrations of glycine, labeled glycine, strychnine, compounds of Formula I, test compounds, and under various conditions are effective to detect and measure inhibition of glycine transporter, including inhibition of glycine transporter mediated by glycine transporter 2 or strychnine sensitive glycine transporters, and to detect and measure compound effects on glycine transporter mediated neuronal activity, including effects on neuronal activity mediated by glycine transporter 2 or strychnine sensitive glycine transporters.

The compounds of Formula I have been demonstrated to inhibit GlyT2 and can be useful in the treatment of certain neurological disorders. Similarly, other compounds which show the same effects on GlyT2 can be useful for the treatment certain neurological disorders. The compounds disclosed in this application can be used as models to discover other new agents that act to inhibit GlyT2. The steps in a process in which these compounds can be utilized to discover new therapeutic agents may be achieved by the following: the compounds may be utilized to validate, optimize, and standardize assays necessary for the discovery of other compounds that inhibit GlyT2. These compounds can be utilized as benchmarks to discover other agents that show improved activity in assays that:

1. Inhibit the glycine transporter;
2. Inhibit the glycine transporter 2;
3. Inhibit strychnine sensitive glycine transporters;
4. Affect glycine transporter mediated neuronal activity
5. Affect GlyT2 mediated neuronal activity
6. Affect strychnine sensitive glycine transporter mediated neuronal activity.

A method to discover agents that show improved activity in assays that inhibit a glycine transporter or that affect glycine transporter mediated neuronal activity comprises the steps of obtaining the results of an assay for the activity of a glycine transporter or of glycine mediated neuronal activity, obtaining the results of the assay in the presence of a plurality of concentrations of a compound of Formula I, obtaining the results of the assay in the presence of a plurality of concentrations of a test compound, comparing the results of the assays, and identifying as an agent that shows improved activity in assays that inhibits a glycine transporter or that affects glycine mediated neuronal activity a test compound from which the results obtained in the assay were improved compared to the results obtained with the compound of Formula I.

Algorithms may be used to compare structures or chemical properties of compounds, such as exemplary compounds and other test compounds. Algorithms may also be used to match structures or chemical properties within libraries of test compounds. In this way, where exemplary compounds or test compounds are known to have certain structures, properties, or activities of interest, compounds can be utilized to discover other compounds or agents that also have such structures, properties, or activities. For example, an activity of interest may be a desired activity in a bioassay. Such algorithms are known; for example, from U.S. Pat. No. 5,567,317 and U.S. Pat. No. 5,587,293, which describe methods for determining the reactivity of candidate compounds with target moieties or receptors. A formula predictive of reactivity with the target receptor may be obtained from a reference set of receptors or from a panel of compounds that are systematically diverse with respect to certain properties. Compounds to be tested in this way can be physically assessed with respect to the reference receptors, the formula applied, and the expected reactivity with the actual target receptor may be predicted. The method of U.S. Pat. No. 5,587,293 does not require the physical presence of the receptor.

The use of such algorithms that compare structures or chemical properties and/or match structures or chemical properties within libraries of test compounds, is effective to discover agents that display activity in bioassays. Such bioassays include bioassays to detect and measure inhibition of glycine transporter, including inhibition of glycine transporter mediated by glycine transporter 2 or strychnine sensitive glycine transporters, and bioassays to detect and measure compound effects on glycine transporter mediated neuronal activity, including effects on neuronal activity mediated by glycine transporter 2 or strychnine sensitive glycine transporters.

Thus, when combined with algorithms that compare structures or chemical properties and/or match structures or chemical properties within libraries of test compounds, the compounds of Formula I can be utilized to discover agents that display activity in bioassays that:

1. Inhibit the glycine transporter;
2. Inhibit the glycine transporter 2;
3. Inhibit strychnine sensitive glycine transporters;
5. Affect glycine transporter mediated neuronal activity
5. Affect GlyT2 mediated neuronal activity
6. Affect strychnine sensitive glycine transporter mediated neuronal activity.

A method to discover agents that display activity in bioassays that inhibit the glycine transporter or affect glycine mediated neuronal activity, comprising applying an algorithm to compare the chemical structures or chemical properties within a library of test compounds with the chemical structure or chemical properties of a compound of Formula I, and identifying as an agent that displays activity in bioassays that inhibits the glycine transporter or affects glycine mediated neuronal activity a test compound determined by the algorithm to have a chemical structure or chemical properties similar to the compound of Formula I.

Algorithms may also be used to compare structures and/or match structures for the purpose of modeling molecular interactions. Such algorithms are known; for example, the methods of U.S. Pat. No. 5,567,317 and U.S. Pat. No. 5,587,293 may be used to compare structures and/or match structures for the purpose of modeling molecular interactions.

The use of such algorithms is effective to discover agents that display activity in bioassays such as bioassays to detect and measure inhibition of glycine transporter, including inhibition of glycine transporter mediated by glycine transporter 2 or strychnine sensitive glycine transporters, and bioassays to detect and measure compound effects on glycine transporter mediated neuronal activity, including effects on neuronal activity mediated by glycine transporter 2 or strychnine sensitive glycine transporters.

Thus, when combined with algorithms that compare structures and/or match structures for the purpose of modeling molecular interactions, these compounds of Formula I can be utilized to discover agents that display activity in bioassays that:

1. Inhibit the glycine transporter;
2. Inhibit the glycine transporter 2;
3. Inhibit strychnine sensitive glycine transporters;
6. Affect glycine transporter mediated neuronal activity
5. Affect GlyT2 mediated neuronal activity
6. Affect strychnine sensitive glycine transporter mediated neuronal activity.

A method to discover agents that display activity in bioassays that inhibit the glycine transporter or affect glycine transporter mediated neuronal activity, comprising applying an algorithm to compare and/or match the chemical structures within a library of test compounds with the chemical structure of a compound of Formula I for the purpose of modeling molecular interactions, and identifying as an agent that displays activity in bioassays that inhibits the glycine transporter or affects glycine transporter mediated neuronal activity a test compound determined by the algorithm to have chemical structure comparable to or matching the compound of Formula I.

EXAMPLES

The Examples which follow serve to illustrate this invention. The Examples are provided to show how to make and use compounds of the invention, and are in no way intended to limit the scope of this invention.

Example 1

3-[(2,6-dichlorophenyl)methylthio]-5-(thien-2-ylthiomethyl)-4-methyl-1,2,4-triazole, 3

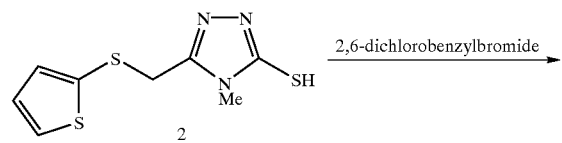

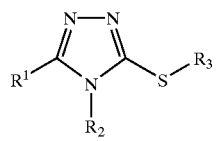

To a solution of 2 (5.012 g, 20.6 mmol) in DMF (100 mL) was added $CsCO_3$ (13.4 g, 25 mmol) with stirring. 2,6-Dichlorobenzylbromide (5.28 g, 22 mmol) was added dropwise with stirring. The reaction was warmed to 80° C. for 24 h. The reaction mixture was cooled then partitioned between EtOAc and 1N HCl. The aqueous layer was extracted twice with EtOAc, and the combined organic layers were washed with 1N HCl, then brine, and then dried over $MgSO_4$. Concentration and chromatography afforded a yellow solid (5.1 g, 66%).

The following compounds were prepared in a similar manner.

| Compound | $R_1$ | $R_2$ | $R_3$ | MW |
|---|---|---|---|---|
| 4 | thien-2-ylthiomethyl | methyl | benzyl | 333.5 |
| 5 | thien-2-ylthiomethyl | methyl | 4-methylbenzyl | 347.5 |
| 6 | thien-2-ylthiomethyl | ethyl | 2,6-dichlorobenzyl | 416.4 |
| 7 | 2-ethyl-5-methyl-3-diazolyl | phenyl | benzyl | 375.5 |
| 8 | phenyl | benzyl | 2,6-dichlorobenzyl | 440.3 |

Example 2

5-[(2,6-dichlorophenyl)methylthio]-2-(pyrazin-2-yl)-1,3,4-thiadiazole, 12

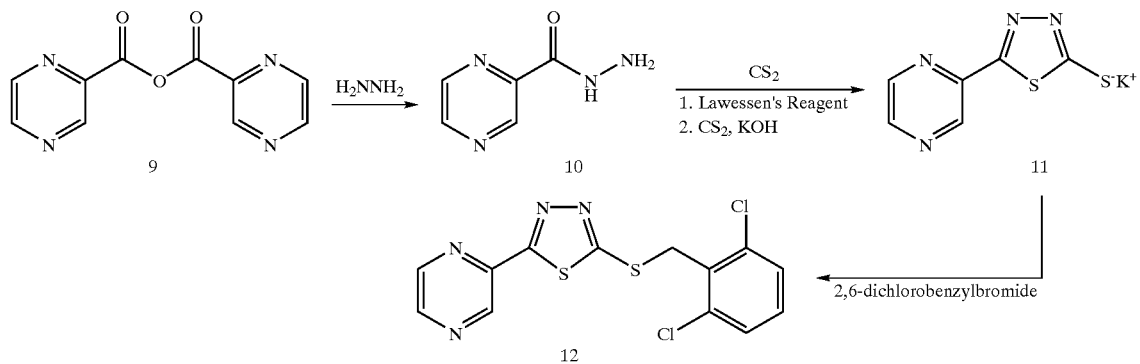

To a solution of 2-pyrazinecarboxylic anhydride (2.2 g, 14.7 mmol) in 20 mL of methylene chloride was added hydrazine in THF (1 M, 15 mL), and the mixture stirred for 24 h. The reaction mixture was concentrated to an oil, diluted with methylene chloride and extracted 3 times with NaHCO$_3$. The organic layer was dried over K$_2$CO$_3$, affording a colorless oil. The resulting hydrazide, 10, was used without further purification. Compound 10 was diluted with Lawesson's reagent (2.9 g, 7.2 mmol) in methylene chloride, and the reaction mixture heated to reflux for 12 h. The mixture was filtered and washed with additional methylene chloride and concentrated in vacuo to a bright yellow solid. This crude material and powdered KOH (1 g, 18 mmol) were stirred in 20 mL of ethanol. Carbon disulfide (0.56 g, 7.4 mmol) was added dropwise, and the reaction mixture was refluxed for 24 h. Volatiles were removed under vacuum, and the resulting solid, 11, was washed with methylene chloride/ethanol to remove soluble impurities. Crude 11 was stirred with DMF and 2,6-dichlorobenzylbromide (1.76 gm, 7 mmol). The reaction was warmed to 80° C. and stirred for 24 h. The mixture was partitioned between methylene chloride and 1N HCl. The aqueous layer was extracted twice with 1N HCl, and the organic layers washed with NaHCO$_3$ and then brine, dried over K$_2$CO$_3$, and then concentrated to a yellow oil. Chromatography afforded an off white solid (1.37 g, 51%).

The following compounds were also prepared in a similar manner:

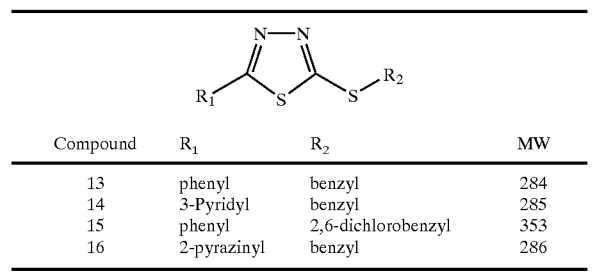

| Compound | R$_1$ | R$_2$ | MW |
|---|---|---|---|
| 13 | phenyl | benzyl | 284 |
| 14 | 3-Pyridyl | benzyl | 285 |
| 15 | phenyl | 2,6-dichlorobenzyl | 353 |
| 16 | 2-pyrazinyl | benzyl | 286 |

Example 3

2,2'-(1,4-butanediyl)bis[5-(benzylthio)-1,3,4-oxadiazole]

Adipic acid, 18, (1.46 g, 10 mmol) was dissolved in methylene chloride, and oxalyl chloride 2.8 g, 22 mmol) was added followed by 1 drop of DMF. The reaction mixture was stirred at room temperature for 2 h, then concentrated under vacuum. The crude oil was dissolved in methylene chloride and reconcentrated under vacuum. The oil was diluted in THF and cooled 0° C. Hydrazine in THF (1 M, 2.2 mL) was added slowly. The mixture was allowed to warm to room temperature overnight, and was then concentrated under vacuum to an oil. The oil was dissolved in methylene chloride, washed with NaHCO$_3$, and dried over K$_2$CO$_3$. The bishydrazide, 19, was dissolved in ethanol and powdered KOH (1.2 g, 22 mmol) was added. Carbon disulfide (1.68 g, 22 mmol) was added dropwise, and the reaction was refluxed for 24 h. The volatiles were removed under vacuum and the residue washed with methylene chloride/ethanol. The solid was dissolved in DMF and treated with benzyl bromide (1.7 g, 10 mmol). The reaction mixture was stirred overnight at 80° C. An aqueous workup and chromatography afforded compound 21 (0.657 g, 7.5%).

Example 4

Inhibition of Glycine Transporter 2

CHO cells expressing rat glycine transporter subtype 2 (GlyT2) were grown in high glucose Dulbecco's modified Eagle's medium supplemented with 10% bovine fetal serum at 37° C. in a 5% CO$_2$ atmosphere. Subconfluent cells growing in 24- or 96-well plates were washed with PBS, and were preincubated at 37° C. for 15 min with uptake buffer (100 mM NaCl, 2 mM KCl, 1 mM CaCl$_2$, 1 mM MgCl$_2$, 10 mM HEPES, pH 7.5) containing sample compounds. Uptake was initiated by adding prewarmed $^3$H-glycine yielding a 10 nM final glycine concentration, and was terminated after 7 min by aspiration of the buffer. Cells were washed 3 times with ice-cold PBS, and radioactivity was determined by scintillation counting using TopCount. GlyT2 inhibitory concentrations for several compounds of Formula I are given below.

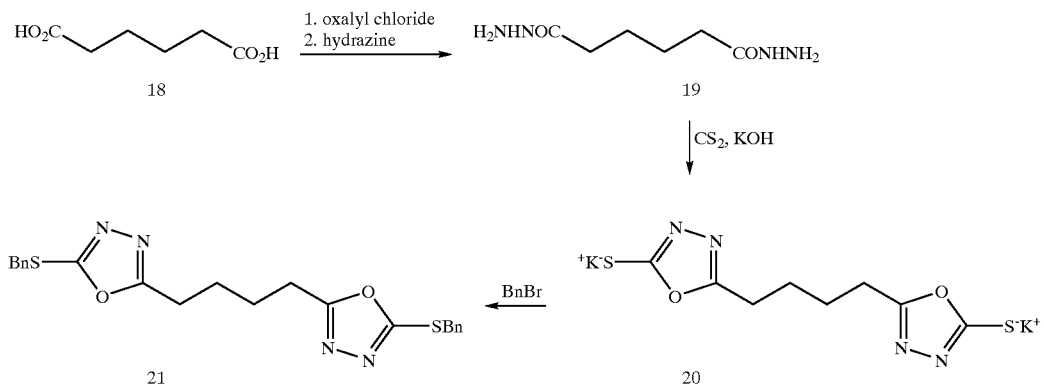

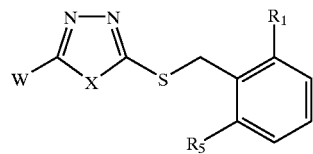

| Cmpd. | W | X | R1 | R5 | GlyT2 Inhib. (μM) |
|---|---|---|---|---|---|
| 4 | (2-thienyl-S-CH2-) | N-Me | Cl | Cl | 8.4 |
| 7 | (1-ethyl-3-methyl-pyrazol-5-yl) | N-Ph | H | H | 6.6 |
| 12 | (pyrazin-2-yl) | S | Cl | Cl | 0.9 |
| 21 | (2-benzylthio-1,3,4-oxadiazol-5-yl-(CH2)4-) | O | H | H | 1.1 |

Example 5

Oral Pharmaceutical Composition Preparation—Solid Dosage Formulation

A pharmaceutical composition for oral administration is prepared by combining the following:

|  | % w/w |
|---|---|
| Compound of the invention | 10% |
| Magnesium stearate | 0.5% |
| Starch | 2.0% |
| hydroxypropylmethylcellulose | 1.0% |
| Microcrystalline cellulose | 86.5% |

The mixture is compressed in a press to form tablets. Alternatively, the mixture is filled into hard gelatin capsules.

Tablets may be coated by applying a suspension of film former (e.g., hydroxypropyl-methylcellulose), pigment (e.g. titanium dioxide) and plasticizer (e.g., diethyl phthalate) and drying the film by evaporation of the solvent. The film coat is 2% to 6% of the tablet weight, e.g. 3% of the tablet weight.

Example 6

Oral Pharmaceutical Composition Preparation—Softgel

A pharmaceutical composition of a compound of the invention suitable for oral administration is prepared by combining the following:

|  | % w/w |
|---|---|
| Compound of the invention | 20% |
| Polyethylene glycol | 80% |

The medicinal compound is dispersed or dissolved in the liquid carrier, and a thickening agent is added. The step of adding the thickening agent is optional. The formulation is then enclosed in a soft gelatin capsule.

Example 7

Pharmaceutical Composition for Parenteral Administration

Pharmaceutical compositions for parenteral administration typically comprise the pharmaceutically active ingredient and physiological saline, such as phosphate buffered saline or other water solution with pH and salt content suitable for introduction into an animal. A pharmaceutical composition for parenteral administration is prepared by combining compound 3 and Dulbecco's Phosphate Buffered Saline (D8662, Sigma Chemical Co. St. Louis, Mo.) as described in the following:

|  | Amount |
|---|---|
| Compound 3 | 1.0% |
| Saline | 99.0% |

The solution is sterilized and sealed in sterile containers.

Although the invention has been described in connection with specific preferred embodiments, it should be understood that the invention as claimed is not limited to such specific embodiments. It will be appreciated by one of ordinary skill in the art that various equivalents of the present invention will be apparent to those skilled in the art without departing from the scope and spirit of the invention, and are within the scope of the following claims.

We claim:

1. A method of treating a disease selected from the group consisting of psychoses, pain, epilepsy, neurodegeneratiVe diseases, stroke, head trauma, multiple sclerosis, spasticity and myoclumus by administering a therapeutically effective amount of a compound of the formula:

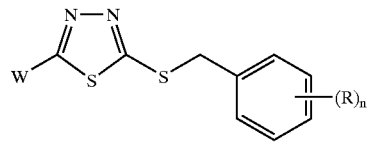

where:

n is 0, 1, or 2;

each R is chlorine; and

W is aryl or heteroaryl, or a pharmaceutically acceptable sale thereof.

2. The method of claim 1 where the compound is selected from

2-[(2,6-dichlorophenyl)methylthio]-5-(pyrazin-2-yl)-1,3,4-thiadiazole, 2-(benzylthio)-5-phenyl-1,3,4-thiadiazole, 2-(benzylthio)-5-(pyridin-3-yl)-1,3,4-thiadiazole, 2-[(2,6-dichlorophenyl)methylthio]-5-phenyl-1,3,4-thiadiazole, and 2-(benzylthio)-5-(pyrazin-2-yl)-1,3,4-thiadiazole.

* * * * *